US008584364B2

(12) United States Patent
Goode et al.

(10) Patent No.: US 8,584,364 B2
(45) Date of Patent: *Nov. 19, 2013

(54) SLITTING TOOL

(75) Inventors: Johnson E. Goode, Maple Grove, MN (US); Ron A. Drake, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/324,722

(22) Filed: Dec. 13, 2011

(65) Prior Publication Data

US 2012/0174410 A1    Jul. 12, 2012

Related U.S. Application Data

(63) Continuation of application No. 12/882,625, filed on Sep. 15, 2010, now Pat. No. 8,074,360, which is a continuation of application No. 11/343,349, filed on Jan. 31, 2006, now Pat. No. 7,950,155.

(51) Int. Cl.
| | |
|---|---|
| *B21F 13/00* | (2006.01) |
| *B26B 27/00* | (2006.01) |
| *A61M 5/178* | (2006.01) |
| *A61B 17/08* | (2006.01) |
| *A61B 17/24* | (2006.01) |
| *A61F 11/00* | (2006.01) |

(52) U.S. Cl.
USPC ............ 30/90.1; 30/280; 30/90.4; 606/161; 606/153; 604/164.05

(58) Field of Classification Search
USPC ............ 30/90.4, 280, 294, 289; 604/164.05, 604/523, 161, 167, 510; 606/161, 167, 153, 606/159, 185
See application file for complete search history.

(56) References Cited

U.S. PATENT DOCUMENTS

| | | | |
|---|---|---|---|
| 2,018,149 A | 10/1935 | Randle et al. | |
| 3,057,232 A | 10/1962 | Cornell | |

(Continued)

FOREIGN PATENT DOCUMENTS

| | | |
|---|---|---|
| WO | WO 01/02047 A1 | 1/2001 |
| WO | WO 2006/085119 A1 | 8/2006 |

(Continued)

OTHER PUBLICATIONS

Medtronic Technical Manual for the 6218RED Guide Catheter Slitter, 2002, 16 pgs.

(Continued)

*Primary Examiner* — Ghassem Alie
*Assistant Examiner* — Bharat C Patel
(74) *Attorney, Agent, or Firm* — Carol F. Barry

(57) ABSTRACT

A tool for slitting an elongate sheath from about an elongate member that is disposed within a longitudinally extending lumen of the sheath includes a longitudinally extending tail portion projecting rearward of a slitting edge and a nose portion of the tool; a lower surface of the nose portion is disposed beneath the slitting edge for engaging a portion of the elongate member. The tail portion of the tool, approximately aligned with the sheath lumen when the lower surface, engages the elongate member and a leading edge of the nose portion is within the sheath lumen, is sized to fit within the sheath lumen after the sheath is slit by the slitting edge. A passageway between the nose portion and the tail portion allows a proximal segment of the elongate member to bend away from the tail portion when the elongate member is engaged by the nose portion.

13 Claims, 6 Drawing Sheets

(56) References Cited

U.S. PATENT DOCUMENTS

| | | | |
|---|---|---|---|
| 3,624,901 A | | 12/1971 | Pettit et al. |
| 3,793,682 A | | 2/1974 | Nelson |
| 3,831,274 A | * | 8/1974 | Horrocks ............... 30/90.4 |
| 3,898,733 A | | 8/1975 | Cormier |
| 4,394,828 A | | 7/1983 | Garbis et al. |
| 4,631,059 A | | 12/1986 | Wolvek et al. |
| 4,687,469 A | | 8/1987 | Osypka |
| 4,997,092 A | | 3/1991 | Dupont |
| 4,997,424 A | * | 3/1991 | Little ..................... 604/161 |
| 5,188,606 A | | 2/1993 | Maloney et al. |
| 5,261,887 A | | 11/1993 | Walker |
| 5,330,460 A | * | 7/1994 | Moss et al. ............ 30/90.4 |
| 5,359,690 A | | 10/1994 | Kaizu et al. |
| 5,687,727 A | | 11/1997 | Kraus et al. |
| 5,873,858 A | * | 2/1999 | Schafer et al. ........... 604/161 |
| D433,929 S | | 11/2000 | Petzl |
| 6,148,521 A | * | 11/2000 | Eslambolchi et al. ...... 30/90.4 |
| 6,159,198 A | | 12/2000 | Gardeski et al. |
| 6,247,235 B1 | | 6/2001 | Lawler |
| 6,277,108 B1 | | 8/2001 | McBroom et al. |
| 6,280,433 B1 | | 8/2001 | McIvor et al. |
| 6,334,253 B1 | | 1/2002 | Cheng |
| 6,368,337 B1 | | 4/2002 | Kieturakis et al. |
| 6,497,681 B1 | * | 12/2002 | Brenner ................. 604/164.05 |
| 6,544,247 B1 | * | 4/2003 | Gardeski et al. ........... 604/510 |
| 7,029,460 B2 | | 4/2006 | Gardeski et al. |
| 7,264,001 B2 | * | 9/2007 | Boutillette et al. ........ 128/898 |
| 7,338,481 B2 | | 3/2008 | Gardeski et al. |
| D576,279 S | | 9/2008 | Bullemer et al. |
| D576,280 S | | 9/2008 | Bullemer et al. |
| 7,462,167 B2 | | 12/2008 | Kratz et al. |
| D608,003 S | | 1/2010 | Bullemer et al. |
| D608,455 S | | 1/2010 | Pasmore et al. |
| 7,950,155 B2 | * | 5/2011 | Goode et al. ............. 30/90.1 |
| 8,074,360 B2 | * | 12/2011 | Goode et al. ............. 30/90.1 |
| 2003/0158565 A1 | | 8/2003 | Gardeski et al. |
| 2003/0181935 A1 | * | 9/2003 | Gardeski et al. ............ 606/167 |
| 2005/0182435 A1 | * | 8/2005 | Andrews et al. ............ 606/172 |
| 2006/0167417 A1 | | 7/2006 | Kratz et al. |
| 2007/0079511 A1 | * | 4/2007 | Osypka .................... 30/90.1 |
| 2007/0175049 A1 | | 8/2007 | Goode et al. |
| 2008/0108972 A1 | | 5/2008 | Andrews et al. |
| 2009/0049698 A1 | | 2/2009 | Drake et al. |
| 2009/0054840 A1 | | 2/2009 | Drake et al. |
| 2009/0071012 A1 | | 3/2009 | Shan et al. |
| 2010/0030154 A1 | | 2/2010 | Duffy |
| 2010/0030161 A1 | | 2/2010 | Duffy |
| 2011/0000089 A1 | | 1/2011 | Goode et al. |

FOREIGN PATENT DOCUMENTS

| | | |
|---|---|---|
| WO | WO 2007/089985 A1 | 8/2007 |
| WO | WO 2009/029558 A2 | 3/2009 |
| WO | WO 2009/029573 A1 | 3/2009 |
| WO | WO 2009/029558 A3 | 9/2009 |
| WO | WO 2010/014419 | 2/2010 |

OTHER PUBLICATIONS

International Search Report for PCT application No. PCT/US2007/060664, May 4, 2007; 2 pgs.

International Preliminary Report on Patentability and Written Opinion for PCT application No. PCT/US2007/060664, Aug. 5, 2008; 6 pgs.

* cited by examiner

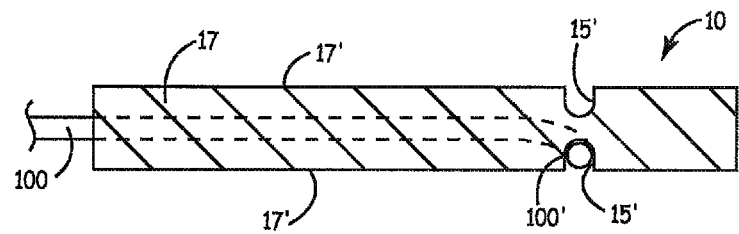
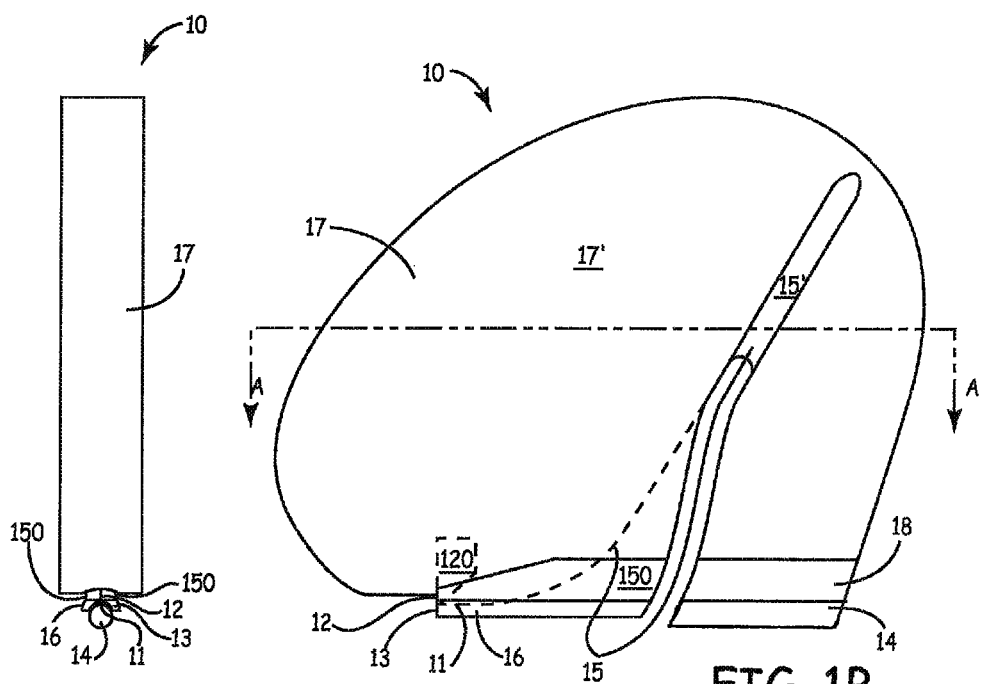

1 …

SLITTING TOOL

This application is a continuation of U.S. patent application Ser. No. 12/882,625, filed on Sep. 15, 2010 (now U.S. Pat. No. 8,074,360), which is a continuation of U.S. patent application Ser. No. 11/343,349 filed on Jan. 31, 2006, now U.S. Pat. No. 7,950,155, both of which are incorporated herein by reference.

FIELD OF THE INVENTION

The present invention pertains to slitting tools and more particularly to slitting tools facilitating removal of an elongate sheath or catheter from about an elongate member disposed therein.

BACKGROUND OF THE INVENTION

Sheaths, or catheters, are commonly used in minimally invasive medical procedures, for example, to provide a pathway for the introduction of elongate medical devices into the vascular system of a patient Many medical devices, introduced in such a manner, through a lumen of the sheath, are intended to indwell within the patient for a prolonged period, for example, extending from a number of days to many years. After the indwelling medical device has been inserted within the lumen of the sheath, for positioning within the patient, it is desirable to remove the sheath from the patient without dislodging the indwelling device.

A number of slitting tools, known to those skilled in the art, are used to remove sheaths from about indwelling medical devices. However, these tools present one or more difficulties to the user, for example, with respect to handling.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 1A-B are an end view and a side plan view, respectively, of a slitting tool according to one embodiment of the present invention.

FIG. 1C is a section view through section line A-A of FIG. 1B.

DETAILED DESCRIPTION OF THE ILLUSTRATED EMBODIMENTS

Figure 2:
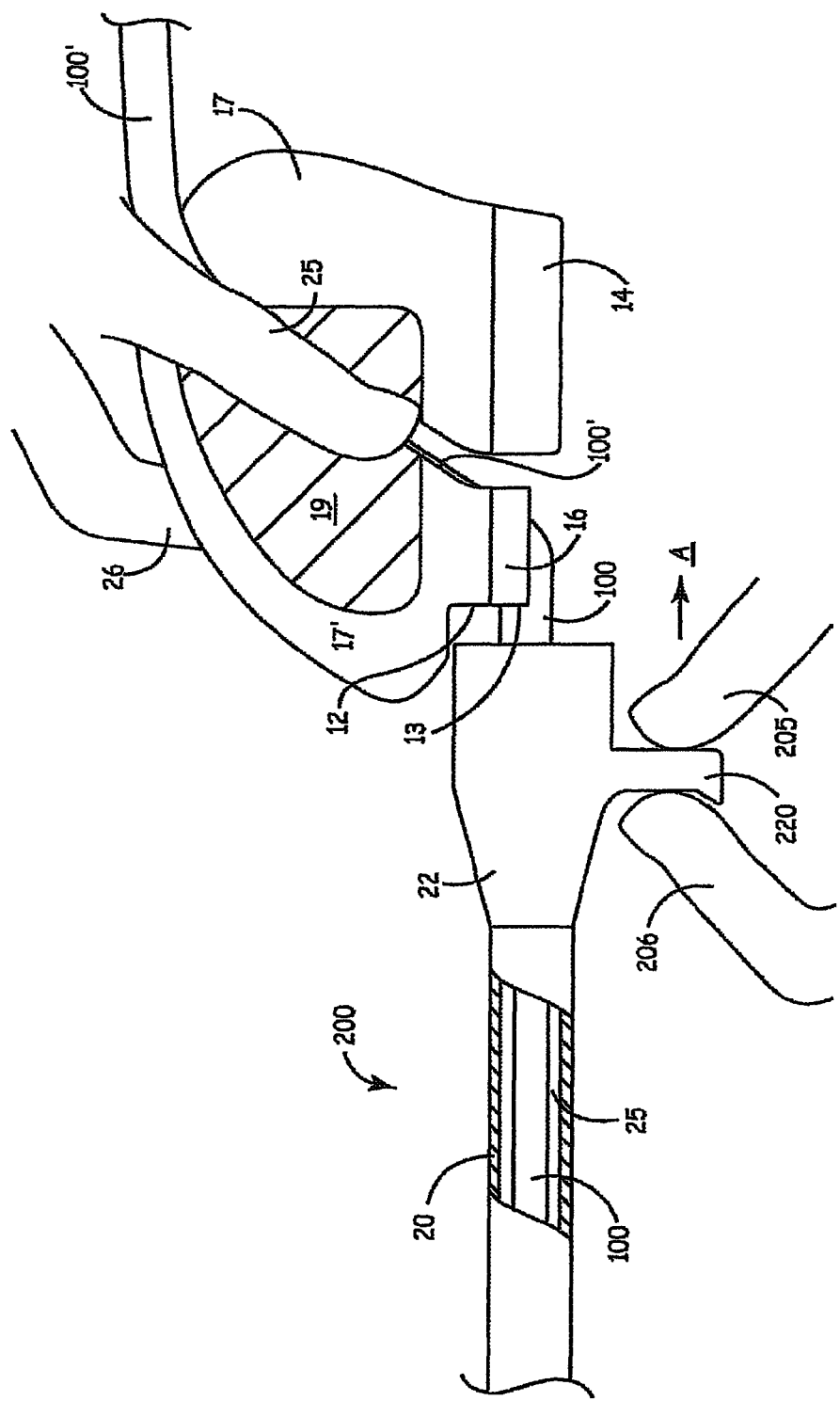
FIG. 2 is a schematic plan view, including, a partial section, depicting a method for using a slitting tool according to some embodiments of the present invention.

The following detailed description is exemplary in nature and is not intended to limit the scope, applicability, or configuration of the invention in any way. Rather, the following description provides practical illustrations for implementing exemplary embodiments of the present invention.

FIGS. 1A-B are an end view and a side plan view, respectively, of a slitting tool 10, according to one embodiment of the present invention; and FIG. 1C is a section view through line A-A of FIG. 1B. FIGS. 1A-C illustrate tool 10 including a nose portion 16, a handle portion 17, a slitting edge 12 extending between nose portion 16 and handle portion 17, a longitudinally extending tail portion 14, and a passageway 15 disposed between nose portion 16 and tail portion 14, and extending upward into handle portion 17. FIGS. 1A-B further illustrate nose portion 16 including a lower surface 11 and a leading edge 13. According to the illustrated embodiment, slitting edge 12 is part of a metallic blade member 120 mounted in handle 17; according to alternate embodiments, slitting edge is an integral part of material forming tool 10 as a whole. Tool 10 may be formed of a rigid plastic, a ceramic, a metallic material or a combination thereof.

According to the illustrated embodiment, lower surface 11 of nose portion 16 is adapted to engage an elongate member 100, and FIG. 1C shows elongate member 100 extending from nose portion 16 into passageway 15 such that a proximal segment 100' of member 100 bends away from tail portion 14. With reference to FIGS. 1B-C, passageway 15 extends from nose portion 16 up into handle 17, being flanked on either side by a sidewall 150; passageway 15 further extends into, grooves 15', which are formed along opposing outer surfaces 17' of handle 17 and either of which can-accommodate segment 100'. An operator, gripping handle 17 of tool 10, may hold proximal segment 100' of elongate member 100 in one of channel grooves 15', as illustrated in FIG. 2.

FIG. 2 is a schematic plan view, including a partial section, depicting a method for using slitting tool 10 according to some embodiments of the present invention. FIG. 2 illustrates elongate member 100, for example, an implantable medical electrical lead, disposed within a lumen 25 of a sheath 200; sheath 200 is shown including a tubular sheath wall 20 terminated at a proximal end by a hub 22. FIG. 2 further illustrates a first thumb 25 and forefinger 26 of an operator holding slitting tool 10 and proximal segment 100' of member 100, while a second thumb 205 and forefinger 206 hold a hub handle 220 to pull sheath 200, per arrow A, against slitting edge 12 of tool 10. Nose portion 16 of tool 10 is shown engaging elongate member 100 while proximal segment 100' bends through passageway 15 that extends along an operator grip zone 19, which, on opposing surfaces 17' of handle 17, is generally located in the zone indicated by cross-hatching. According to the illustrated embodiment, tail portion 14 of tool 10 is approximately aligned with sheath lumen 25 and is sized to fit within sheath lumen 25, when slit, so that tail portion 14 will ride within sheath lumen 25 after slitting edge 12 cuts through hub and sheath wall 20. According to some embodiments, tail portion 14 further includes a profile closely conforming with slit sheath lumen 25, for example as illustrated in FIG. 3B.

Figure 3A:
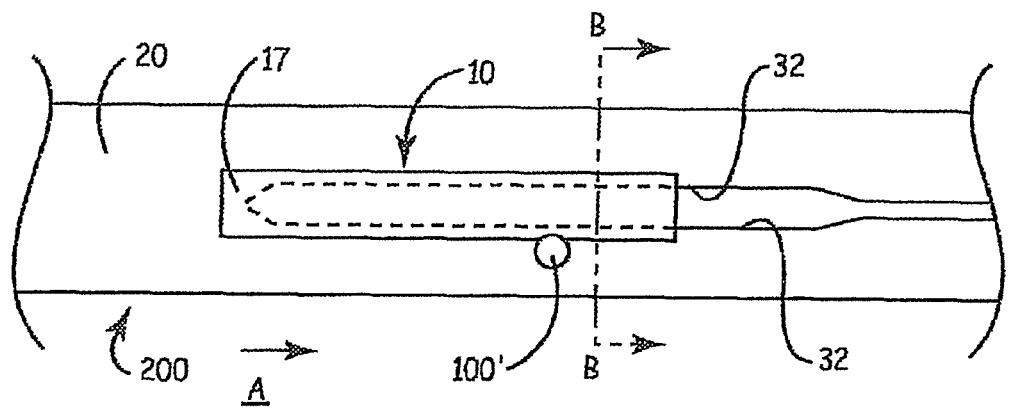
FIG. 3A is a top view of the slitting tool, shown in FIGS. 1A-C, cutting through a portion of a sheath wall.
Figure 3B:
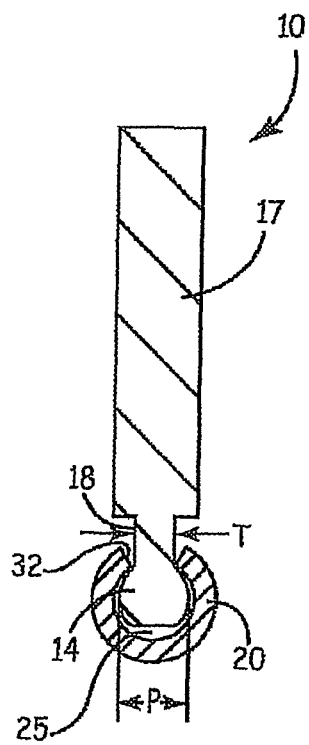
FIG. 3B is a section view through section line B-B of FIG. 3A.

FIG. 3A is a top view of the slitting tool, shown in FIGS. 1A-C, cutting through a portion of sheath wall 20; and FIG. 3B is a section view through section line B-B of FIG. 3A. FIGS. 3A-B illustrate sheath 200 having been pulled, per arrow A, so that sheath wall 20 has been slit by tool slitting edge 12 (FIGS. 1A-B and 2) and tool tail portion 14 is disposed within lumen 25, downstream of slitting edge 12; slit edges 32 of sheath wall 20 emanate from slitting edge 12 beneath tool handle 17, shown by dashed lines, and extend downstream of tool 10; fingers 25, 26 and associated hand of the operator holding tool 10 (FIG. 2) are not shown so that the view of tool 10 and slit edges 32 of sheath wall 20 is not obstructed. FIG. 3B further illustrates a profile of tail portion 14, formed by a continuous exterior surface extending thereabout, which closely mates with slit sheath lumen 25; a width P of tail portion 14 may be approximately equal to or slightly greater than a pre-slit diameter of sheath lumen 25, or may be up to two times greater than the pre-slit diameter of lumen 25. FIG. 3B further illustrates tool 10 including a shank 18 joining handle 17 to tail portion 14; according to some embodiments, a thickness T of shank 18 is greater than approximately 0.01 inch and less than width P of tail portion 14.

According to embodiments of the present invention, tail portion 14 may serve to stabilize tool 10 as it cuts through sheath wall 20 and may further prevent slit edges 32 from collapsing toward one another in a way which may cause slit sheath lumen 25 to 'grab' elongate member 100, as sheath 200 is pulled, per arrow A, thereby dislodging a distal end of member 100. An effective length of tail portion 14, for stabilizing tool 10 as it cuts through sheath wall 20, may be approximately equal to or greater than ½ inch. Although, in FIG. 2, tail portion 14 is illustrated extending proximally from operator grip zone 19 of handle portion 17, embodiments of the present invention are not so limited.

Figure 4A:
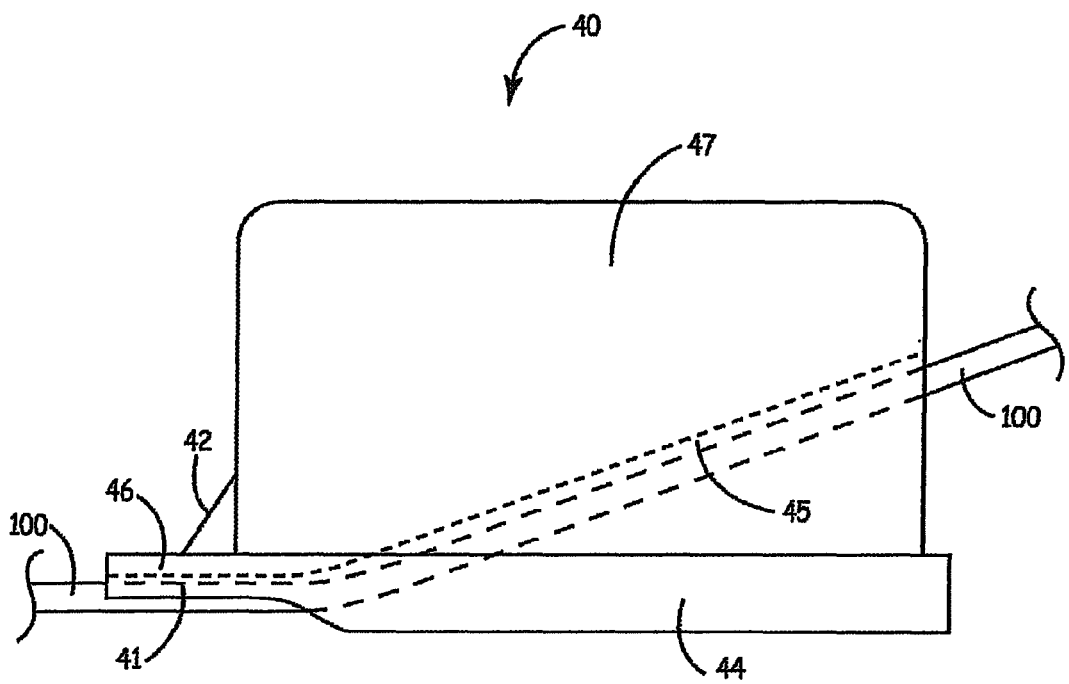
FIGS. 4A-B are a side plan view and an end view of a slitting tool according to another embodiment of the present invention.
Figure 4B:
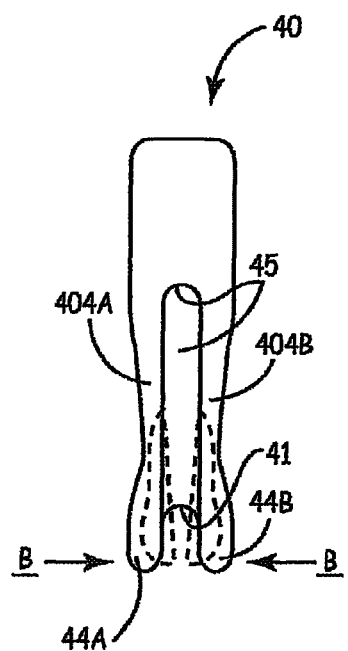

FIGS. 4A-B are a side plan view and an end view of a slitting tool 40 according to another embodiment of the present invention. FIGS. 4A-B illustrate tool 40 including a nose portion 46, a handle portion 47, a slitting edge 42 extending between nose portion 46 and handle portion 47, and a longitudinally extending tail portion 44. FIGS. 4A-B further illustrate nose portion 46 including a lower surface 41 extending from a leading edge 43 to a passageway 45 that extends from between nose portion 46 and tail portion 44, upward into handle portion 47. According to the illustrated embodiment, to facilitate loading of elongate member 100 into passageway 45, for example, as shown in FIG. 4A, tail portion 44 is split into a first leg 404A and a second leg 404B. FIG. 4B shows each leg 404A, B including a foot 44A and 44B, respectively; feet 44A, B together form a tail profile, to mate with a slit lumen of a sheath or catheter, when legs are forced, per arrows B, together, as shown with dashed lines; the resulting profile is similar to that of solid tail 14 illustrated in FIG. 3B. Legs 404A, B would be forced together in such a way when a sheath is pulled past slitting edge 42 of tool 40 such that tail 44 is enclosed by the slit lumen of the sheath.

Figure 5A:
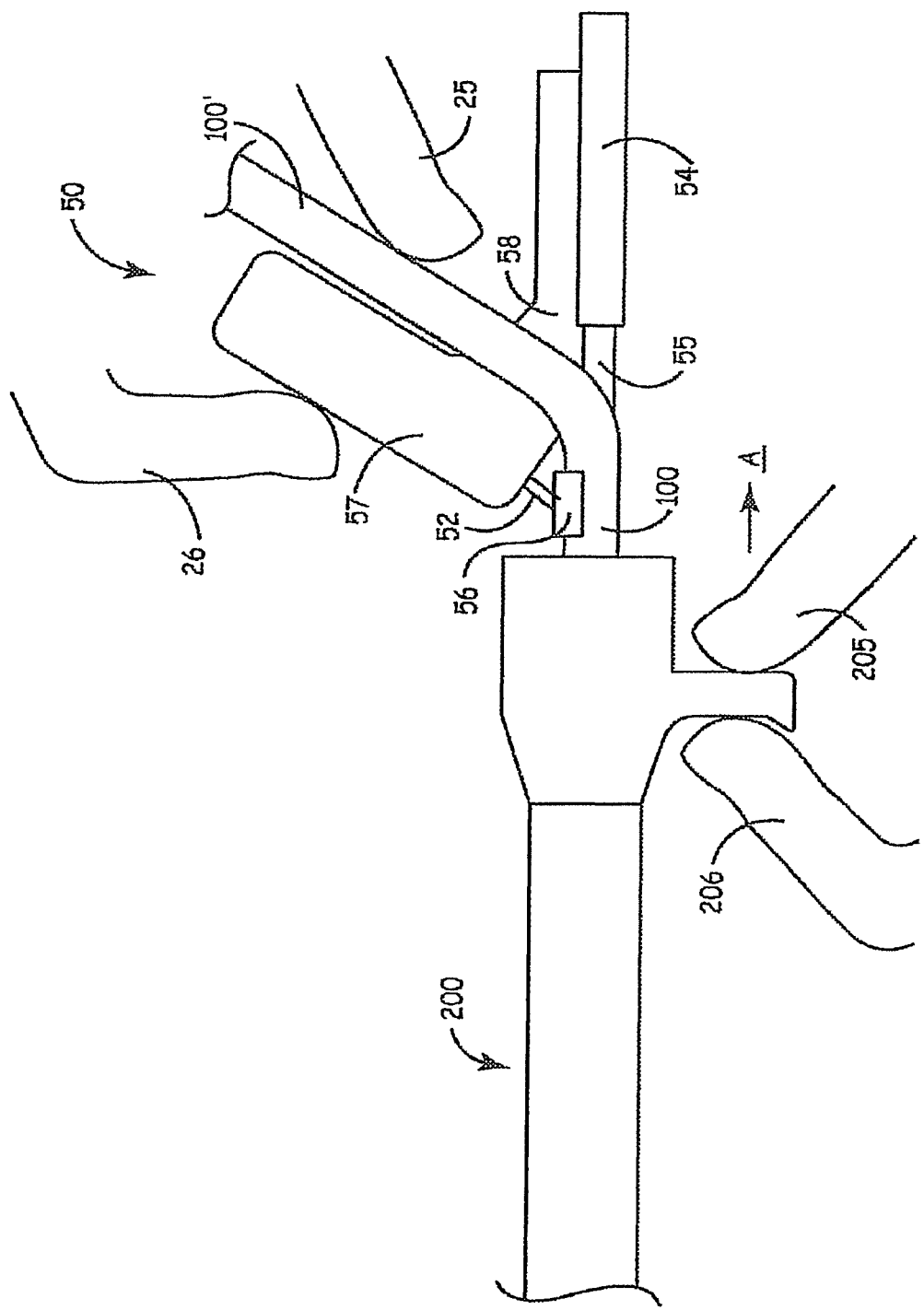
FIG. 5A is a schematic showing an alternate embodiment of a slitting tool in a position for slitting a sheath.
Figure 5B:
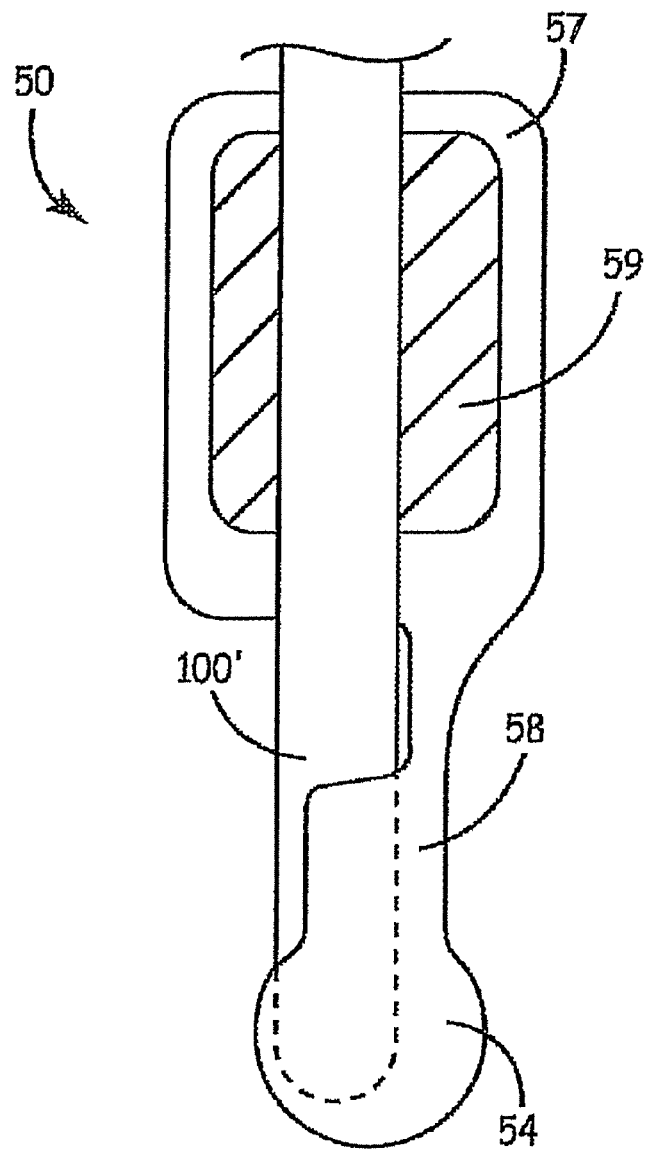
FIG. 5B is an end view of FIG. 5A.

FIG. 5A is a schematic showing an alternate embodiment of a slitting tool 50 in a position for slitting sheath 200; and FIG. 5B is an end view of FIG. 5A. FIG. 5A illustrates tool 50 including a nose portion 56, a handle portion 57, a slitting edge 52, extending between nose portion 56 and handle portion 57, and a longitudinally extending tail portion 54, which is joined to handle portion 57 by a shank 58. FIG. 5A further illustrates nose portion 56 engaging elongate member 100 and a passageway 55, disposed between nose portion 56 and tail portion 54, allowing proximal segment 100' of elongate member 100 to bend away from tail portion 54. According to the illustrated embodiment, fingers 25 and 26, associated with the hand of the operator, hold segment 100' against an operator grip zone 59 of handle 57, the extent of which generally corresponds to the cross-hatched area shown in FIG. 5B.

In the foregoing detailed description, the invention has been described with reference to specific embodiments. However, it may be appreciated that various modifications and changes can be made without departing from the scope of the invention as set forth in the appended claims.

The invention claimed is:

1. A tool for slitting an elongate sheath from about an elongate member disposed within a lumen of the sheath, the tool comprising:
a slitting edge directed forward to slit an elongate sheath;
a handle portion carrying the slitting edge, wherein the handle portion comprises opposing outer surfaces, wherein at least one of the opposing outer surfaces has a groove defined therein to receive at least a portion of an elongate member when an elongate sheath is being slit; and
a nose portion extending from a leading edge proximate the slitting edge to a rear portion thereof, wherein the nose portion comprises:
a lower surface open downward to contact a portion of an elongate member when an elongate sheath is being slit, wherein the lower surface proximate the leading edge defines a linear passageway along an axis in which an elongate member is located when an elongate sheath is being slit, and further wherein the rear portion of the nose portion defines a non-linear passageway deviating from the axis and extending to the groove defined in the at least one opposing outer surface of the handle portion to allow a portion of an elongate member to bend upward and away from the axis when an elongate sheath is being slit; and
one or more separation surfaces extending along at least a portion of the linear passageway and at least to a location rearward of the deviation of the non-linear passageway from the axis of the linear passageway to separate a portion of an elongate member received within the non-linear passageway proximate the linear passageway from the slit edges of an elongate sheath when an elongate sheath is being slit.

2. The tool of claim 1, wherein the one or more separation surfaces comprise one or more outwardly facing surfaces flanking the linear passageway extending along the axis and at least a portion of the non-linear passageway extending upward into the handle portion, the one or more outwardly facing surfaces comprising one or more sheath contact surfaces extending linearly along the axis opposite the lower surface and at least to a location rearward of the deviation of the non-linear passageway from the axis of the linear passageway, wherein the one or more sheath contact surfaces separate the portion of an elongate member received within the non-linear passageway proximate the linear passageway bending upward and away from the axis and the slit edges of an elongate sheath when an elongate sheath is being slit.

3. The tool of claim 2, wherein the one or more outwardly facing surfaces flanking the linear passageway extending along the axis and at least a portion of the non-linear passageway extending upward into the handle portion comprise sidewalls flanking either side of the non-linear passageway extending upward into the handle portion.

4. The tool of claim 1, wherein at least the lower surface proximate the leading edge of the nose portion defining the linear passageway comprises a concave surface for receiving a portion of an elongate member when the elongate sheath is being slit, and further wherein the one or more separation surfaces comprise convex surfaces flanking either side of the linear passageway and extending along the axis to a location rearward of the deviation of the non-linear passageway from the axis of the linear passageway.

5. The tool of claim 1, wherein each of the opposing outer surfaces have a groove defined therein for receiving at least a portion of an elongate member when an elongate sheath is being slit, the groove on each opposing outer surface being located such that the fingers of the operator holding the handle portion also hold an elongate member in the groove when an elongate sheath is being slit, and further wherein the non-linear passageway extending upward into the handle portion extends to the groove defined in each of the opposing outer surfaces.

6. The tool of claim 1, wherein the slitting edge is mounted in the handle.

7. The tool of claim 1, wherein the tool further comprises a longitudinally extending tail portion projecting rearward of the slitting edge and rear portion of the nose portion, the tail portion extending between a first end and a second end downwardly from a portion of the handle portion and separated from the rear portion by the non-linear passageway, the tail portion being approximately aligned with the axis of the linear passageway and sized to fit within a sheath lumen after an elongate sheath is slit by the slitting edge such that the tail portion mates within the slit sheath lumen and prevents the slit edges of the elongate sheath from collapsing toward one another.

8. A method of slitting an elongate sheath from about an elongate member disposed within a longitudinally extending lumen of the elongate sheath, the method comprising:
   providing a slitting tool, wherein the slitting tool comprises:
      a slitting edge directed forward to slit an elongate sheath;
      a handle portion carrying the slitting edge, wherein the handle portion comprises opposing outer surfaces, wherein at least one of the opposing outer surfaces has a groove defined therein to receive at least a portion of an elongate member when an elongate sheath is being slit; and
      a nose portion extending from a leading edge proximate the slitting edge to a rear portion thereof, wherein the nose portion comprises:
         a lower surface open downward to contact a portion of an elongate member when an elongate sheath is being slit, wherein the lower surface proximate the leading edge defines a linear passageway along an axis in which an elongate member is located when an elongate sheath is being slit, and further wherein the rear portion of the nose portion defines a non-linear passageway deviating from the axis and extending to the groove defined in the at least one opposing outer surface of the handle portion to allow a portion of an elongate member to bend upward and away from the axis when an elongate sheath is being slit; and
         one or more separation surfaces extending along at least a portion of the linear passageway and at least to a location rearward of the deviation of the non-linear passageway from the axis of the linear passageway to separate a portion of an elongate member received within the non-linear passageway proximate the linear passageway from the slit edges of an elongate sheath when an elongate sheath is being slit;
   receiving a portion of an elongate member in the linear passageway and in contact with the lower surface of the nose portion and receiving one or more other portions of the elongate member in the non-linear passageway and in the groove defined in the at least one opposing outer surface such that the elongate member is bent upward and away from the axis of the linear passageway;
   holding the handle portion with one or more fingers against at least the elongate member received in the groove; and
   pulling the elongate sheath against the slitting edge to slit the elongate sheath.

9. The method of claim 8, wherein the one or more separation surfaces comprise one or more outwardly facing surfaces flanking the linear passageway extending along the axis and at least a portion of the non-linear passageway extending upward into the handle portion, the one or more outwardly facing surfaces comprising one or more sheath contact surfaces extending linearly along the axis opposite the lower surface and at least to a location rearward of the deviation of the non-linear passageway from the axis of the linear passageway, wherein the one or more sheath contact surfaces separate the portion of the elongate member received within the non-linear passageway proximate the linear passageway bending upward and away from the axis and the slit edges of the elongate sheath when the elongate sheath is being slit.

10. The method of claim 9, wherein the one or more outwardly facing surfaces flanking the linear passageway extending along the axis and at least a portion of the non-linear passageway extending upward into the handle portion comprise sidewalls flanking either side of the non-linear passageway extending upward into the handle portion.

11. The method of claim 8, wherein at least the lower surface proximate the leading edge of the nose portion defining the linear passageway comprises a concave surface for receiving the portion of the elongate member when the elongate sheath is being slit, and further wherein the one or more separation surfaces comprise convex surfaces flanking either side of the linear passageway and extending along the axis to a location rearward of the deviation of the non-linear passageway from the axis of the linear passageway.

12. The method of claim 8, wherein the tool further comprises a longitudinally extending tail portion projecting rearward of the slitting edge and rear portion of the nose portion, the tail portion extending between a first end and a second end downwardly from a portion of the handle portion and separated from the rear portion by the non-linear passageway, the tail portion being approximately aligned with the axis of the linear passageway and sized to fit within the sheath lumen after the elongate sheath is slit by the slitting edge such that the tail portion mates within the slit sheath lumen and prevents the slit edges of the elongate sheath from collapsing toward one another.

13. The method of claim 8, wherein the slitting edge is mounted in the handle.

\* \* \* \* \*